(12) United States Patent
Malofsky et al.

(10) Patent No.: US 8,106,234 B2
(45) Date of Patent: Jan. 31, 2012

(54) METHYLIDENE MALONATE PROCESS

(75) Inventors: Bernard M. Malofsky, Bloomfield, CT (US); Chris Mariotti, Unionville, CT (US)

(73) Assignee: OptMed, Inc, Woodmere, NY (US)

( * ) Notice: Subject to any disclaimer, the term of this patent is extended or adjusted under 35 U.S.C. 154(b) by 0 days.

(21) Appl. No.: 12/774,817

(22) Filed: May 6, 2010

(65) Prior Publication Data

US 2010/0286439 A1 Nov. 11, 2010

Related U.S. Application Data

(60) Provisional application No. 61/215,610, filed on May 7, 2009, provisional application No. 61/215,578, filed on May 7, 2009, provisional application No. 61/291,898, filed on Jan. 3, 2010.

(51) Int. Cl.
*C07C 69/74* (2006.01)
*C07C 61/00* (2006.01)
*C07C 62/30* (2006.01)

(52) U.S. Cl. ........................................ 560/128; 562/510

(58) Field of Classification Search ................. None
See application file for complete search history.

(56) References Cited

U.S. PATENT DOCUMENTS

| | | | |
|---|---|---|---|
| 2,313,501 A | 3/1943 | Bachman et al. | |
| 2,330,033 A | 9/1943 | D'Alelio | |
| 3,197,318 A | 7/1965 | Halpern et al. | |
| 3,221,745 A | 12/1965 | Coover et al. | |
| 3,523,097 A | 8/1970 | Coover et al. | |
| 3,591,676 A | 7/1971 | Hawkins et al. | |
| 3,758,550 A | 9/1973 | Eck et al. | |
| 4,049,698 A | 9/1977 | Hawkins et al. | |
| 4,056,543 A | 11/1977 | Ponticello | |
| 4,160,864 A | 7/1979 | Ponticello et al. | |
| 4,291,171 A | 9/1981 | Baum et al. | |
| 4,840,949 A * | 6/1989 | Korbonits et al. | 514/234.2 |
| 4,931,584 A | 6/1990 | Bru-Magniez et al. | |
| 5,142,098 A | 8/1992 | Bru-Magniez et al. | |
| 5,328,687 A | 7/1994 | Leung et al. | |
| 5,514,371 A | 5/1996 | Leung et al. | |
| 5,550,172 A | 8/1996 | Regula et al. | |
| 6,106,807 A | 8/2000 | Albayrak et al. | |
| 6,211,273 B1 | 4/2001 | Bru-Magniez et al. | |
| 6,420,468 B2 | 7/2002 | Bru-Magniez et al. | |
| 6,440,461 B1 | 8/2002 | Bru-Magniez et al. | |
| 6,512,023 B1 | 1/2003 | Malofsky et al. | |
| 6,610,078 B1 | 8/2003 | Bru-Magniez et al. | |
| 6,750,298 B1 | 6/2004 | Bru-Magniez et al. | |
| 2001/0034300 A1 * | 10/2001 | Yurugi et al. | 502/300 |
| 2004/0076601 A1 | 4/2004 | Bru-Magniez et al. | |

OTHER PUBLICATIONS

Diethyl Methylenemalonate. Wayne Feely et al. Organic Syntheses, Coll vol. 4, p. 298; vol. 38 p. 22 (1958).
DI-tert-Butyl Methylenemalonate. Paloma Ballesteros et al. Organic Syntheses, Coll. vol. 7, p. 142 (1990); vol. 64, p. 63 (1986).
2-Methylenedodecanoic Acid. C. Freeman Allen et al. Organic Syntheses, Coll. Vol. 4, p. 616 (1963); vol. 38, p. 47 (1958).
Sustained delivery of growth factors from methylidene malonate 2.1.2-based polymers. Laurent Desire et al. Biomaterials 27 (2006) 2609-2620.
Biocompatible poly(methylidene malonate)-made materials for pharmaceutical and biomedical applications. Pascal Breton et al European Journal of Pharmaceutics and Biopharmaceutics XXX (2007)XXX-XXX.
Preparation and Characterization of Novel Poly(methylidene Malonate 2.1.2.)-made Nanoparticles Francois Lescure et al Pharmaceutical Research, vol. 11, No. 9, 1994, 1270-1277.
Synthesis and micellization of amphiphilic poly(ethylene oxide)-block-poly(methylidene malonate 2.1.2.) diblock copolymers. Virginie Larras et al Macromol, Rapid Commun. 2000,21,1089-1092.
Structure elucidation of methylidene malonate 2.1.2 cyclic trimers with mass spectrometry, liquid chromatography and nuclear magnetic resonance investigations. A. Salvador et al Journal of Pharmaceutical and Biomedical Analysis 22 (2000) 165-174.

* cited by examiner

*Primary Examiner* — Daniel Sullivan
*Assistant Examiner* — Jennifer C Sawyer
(74) *Attorney, Agent, or Firm* — Edward K Welch, II; IP&L Solutions

(57) ABSTRACT

An improvement in the production of methylidene malonates is attained by use of specific reaction phase and/or separation phase polymerization inhibitors and combinations thereof.

31 Claims, No Drawings

METHYLIDENE MALONATE PROCESS

RELATED APPLICATION

This application is a non-provisional application and claims the benefit of U.S. Provisional Patent Application Ser. Nos. 61/215,610 and 61/215,578, both of which were filed on May 7, 2009 and entitled Improved Methylidene Malonate Process, and the benefit of U.S. Provisional Patent Application Ser. No. 61/291,898, filed Jan. 3, 2010, entitled Methylidene Malonate Process, all of which are hereby incorporated herein by reference in their entirety.

FIELD OF THE INVENTION

The present invention relates to an improved process for the production of methylidene malonates as well as the methylidene malonates produced thereby and the use thereof. Specifically, the present invention provides for a high-temperature pyrolysis-free method for the preparation of methylidene malonates from diene-malonate adducts which method avoids the need for diluents or like solvents or liquid media in the stripping step.

BACKGROUND

Methylidene malonates are compounds having the general formula (I):

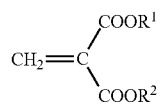
(I)

wherein $R^1$ and $R^2$ may be the same or different and represent H or a $C_1$ to $C_{18}$ hydrocarbon group or heterohydrocarbon group having one or more nitrogen, halogen, or oxygen atoms; provided that $R^1$ and $R^2$ are not both H. Such compounds have been known for well over half a century and their value in both organic synthesis and polymer chemistry is well known. Similarly, the use of these compounds as or as a component of adhesives, including skin bonding adhesive; molding materials; and the like is equally well known. Yet, despite all the promise, these compounds have found limited commercial success owing to the difficulty of their production; the poor, though improving, yet still erratic, yields; and the general instability of these compounds.

Numerous processes have been developed for the production of methylidene malonates having a formula similar to or falling within the formula of formula (I) above. Two of the earliest methods for the production of methylene dialkyl malonates, the simplest of the methylidene malonates, were the iodide method in which methylene iodide was reacted with dialkyl malonates and the formaldehyde method in which formaldehyde was reacted with dialkyl malonates in the presence of a base, in solution in alcohol solvents. The former was unsatisfactory due to very low yield and expensive starting materials. The latter, though periodically giving better yields than the iodide process, gave relatively poor yields and, more critically, was widely inconsistent from batch to batch, even under the same conditions.

Despite this inconsistency, early efforts continued to focus on the formaldehyde method. One of the most widely practiced formaldehyde methods consisted of reacting diethyl malonate with formaldehyde in glacial acetic acid in the presence of a metal acetate catalyst to produce the diethyl methylidene malonate. The latter was subsequently recovered by distillation following removal of the catalyst by filtration and separating off the solvent. These efforts continued to frustrate and various modifications and iterations of this basic process were developed all in an effort to improve the consistency and yields associated therewith.

Bachman et. al. (U.S. Pat. No. 2,313,501) taught the reaction of a $C_1$-$C_5$ dialkyl malonate with formaldehyde in the presence of an alkali metal salt of a carboxylic acid, in solution in a substantially anhydrous carboxylic acid solvent, followed by fractional distillation to separate the desired product. Bachman et. al. indicate that their process is advantageously carried out in the presence of inhibitors of the polymerization of monomeric vinyl compounds. Suitable inhibitors are said to include the copper salts such as copper chloride and, especially, copper salts of carboxylic acids such as cupric acetate, iron salts such as ferric acetate, and phenols, such as hydroquinone. These are added to the solution mix before the addition of the malonate.

Although Bachman et. al. reported yields of up to 72%, the results presented are conversion rates, not yields. Looking at the actual yields of the process, Bachman et. al.'s best performance was a yield of 43% with all others being less than 25%. Though Bachman et. al. speak of high purity and the ability to recover pure material, they never present any details or data as to what those purities or recoveries were. In any event, Bachman et. al. reported that the isolated product, upon standing, polymerized in a day to several weeks time depending upon the purity of the isolated material, which polymer was then heated to facilitate the reversion of the polymer to the monomer.

D'Alelio (U.S. Pat. No. 2,330,033), on the other hand, alleged that such processes were erratic and more often produced yields that averaged 10 to 12 percent. D'Alelio espoused an improved process with yields on the order of 30% and higher by reacting a malonic acid ester with formaldehyde in a ratio of one mole of the former to at least one mole of the latter under alkaline conditions and, in most cases, in the presence of a polymerization inhibitor such as copper, copper acetate, hydroquinone, resorcinol, or catechol, to form a methylol derivative. The methylol derivative is then acidified to a pH below 7.0 using a suitable organic or inorganic acid in order to retard further reaction. The acidified mass is then dehydrated to form the corresponding methylidene malonate which is subsequently separated by distillation.

Coover et. al. (U.S. Pat. Nos. 3,221,745 and 3,523,097) took another approach to the formation of the methylidene malonates, electing to begin with a preformed dialkyl alkoxymethylenemalonate. In accordance with their process, the olefinic double bond of the latter compound was subjected to hydrogenation in the presence of a hydrogenation catalyst and the hydrogenated compound was then subject to pyrolysis in the presence of a phosphorous pentoxide inhibitor to strip off the alcohol to produce the methylene malonate. The resultant mass was then subjected to vacuum distillation at low temperature to separate an allegedly high purity methylidene malonate, though with a low yield. According to Coover et. al., the use of low temperature distillation is said to prevent the contamination of the monomer with pyrolytic products that commonly result from high temperature distillation. These high purity monomers are said to be especially important for surgical applications.

In discussing the critical need for high purity materials, Coover et. al. draw particular attention to the extreme sensitivity of their monomers to the presence of even small amounts of acidic and basic impurities, the former inhibiting polymerization leading to sluggish and ineffective adhesive activity and the latter accelerating polymerization leading to unstable and useless products. They indicate that the amount of such impurities should not exceed 100 ppm, preferably not more than 10 ppm. Unfortunately, other than discussing its limitations with respect to the acidic and basic impurities, and despite its contention of high purity materials, Coover et. al. never provide any data pertaining to the purity of their materials. Clearly, though, they are not "pure" materials inasmuch as they, like the others before them and since, require redistillation of the "pure" distillate.

Additionally, although suggesting that their high purity materials "have reasonably good" stability when stored in bulk, they recommend the addition of low levels, 0.0001 to 0.01 weight percent, of a polymerization inhibitor to the monomer materials in order to increase storage stability. Suitable polymerization inhibitors are said to include sulfur dioxide, hydroquinone, nitric oxide, organic acids, boron trifluoride, hydrogen fluoride, stannic chloride, ferric chloride, and organic anhydrides. To assist with cure, particularly cure speed, Coover et. al. also suggest the addition of cure accelerators or catalysts to their formulated adhesives, but cautions against adding them too early as they would cause premature polymerization.

Despite the erratic nature of the aforementioned processes, there were continued efforts to find improved processes for the production of methylidene malonates with a focus on more consistent and reliable processes with improved yields and higher purity. These effort focused not only on the simple methylidene malonates of the early art but also on finding new routes that allowed for the formation of a broader array of methylidene malonates, including symmetrical and asymmetrical species as well as those whose ester functionality was more complex, e.g., having a higher carbon number, unsaturation, heteroatoms and the like.

Eventually, such efforts led to multi-step processes in which certain unsaturated molecules served as a platform for the formation of intermediate adducts from which the methylidene malonates were subsequently stripped and recovered. For example, Hawkins et. al. (U.S. Pat. No. 4,049,698) found that certain malonic diesters could be reacted with formaldehyde and a linear, conjugated diene in the presence of a primary, secondary or tertiary amine at about reflux temperature to form an intermediate adduct that could then be readily pyrolyzed at temperatures in excess of 600° C. to split off the desired methylidene malonate. Similarly, Ponticello (U.S. Pat. No. 4,056,543) and Ponticello et. al. (U.S. Pat. No. 4,160,864) developed processes by which asymmetrical methylene malonates, especially methyl allyl methylene malonate, were prepared from previously formed norbornene adducts, the latter having been prepared by the Diels-Alder reaction of an alkyl acrylate with cyclopentadiene at room temperature or with heating or use of a Lewis catalyst. The so formed monoester norbornene adducts were then reacted with an electrophile material in the presence of an alkyl-substituted lithium amide complex to form the diester adduct and subsequently pyrolyzed at a temperature of 400° C. to 800° C. at a pressure of 1 mm to 760 mm Hg in an inert atmosphere to strip off the desired methylene malonates. These efforts, despite their gains in yield and/or purity, still failed to achieve commercial success.

Citing numerous disadvantages of the foregoing processes, which disadvantages were said to make them difficult, if not impossible, to adapt to industrial scale, Bru-Magniez et. al. (U.S. Pat. Nos. 4,932,584 and 5,142,098) developed a process whereby anthracene adducts were prepared by reacting mono- or di-malonic acid ester with formaldehyde in the presence of anthracene, most preferably in a non-aqueous solvent medium in the presence of select catalysts. According to Bru-Magniez et. al., the anthracene adducts were said to be readily produced in high yields with the desired methylidene malonates obtained by stripping them from the anthracene adduct by any of the known methods including heat treatment, thermolysis, pyrolysis or hydrolysis; preferably heat treatment in the presence of maleic anhydride, further in the presence of a suitable solvent or liquid medium. The resultant crude products were then subjected to multiple distillations, preferably lower temperature distillations under vacuum, to recover the purified methylidene malonate. Despite the claim to high yields, their crude yields were generally in the range of 21-71%, more importantly, nothing is said with respect to the purity of the material obtained.

Based on conversations with the successors to the Bru-Magniez technology, efforts to commercially produce the material have met with great difficulty owing to the high instability of the overall production process and final products. Indeed, they reported a high failure rate: of the limited batches that actually survived through crude distillation, the resultant products had to be stored in a freezer even after stabilizing with upwards of 50,000 ppm $SO_2$ due to their high instability and spontaneous polymerization. Indeed, our own attempts to follow the prior art processes, including the Bru-Magniez process, most often resulted in failure owing to sublimation of the paraformaldehyde, a failure to produce the desired product (as evidenced by a lack of double bonds in the reaction product), and, more frequently, polymerization of the reaction mix and/or the crude yield. Even when a successful run was realized, it has now been found that the purity of the materials was quite low. Though the traditional analytical tests employed, including, the boiling point, fraction temperature, and refractive index suggests good yield and purity, further, more sophisticated analysis has found that these reaction products actually contained a number of analogs of the desired methylidene malonate, in addition to the desired material, as well as various byproducts. For example, in our efforts to produce 1-ethoxycarbonyl-1-ethoxycarbonyl methylene oxycarbonyl ethane (the 2.1.2 monomer), we found that besides the 2.1.2 monomer, the reaction products, even after initial separation and distillation, contained substantial amounts of the di-substituted and unsubstituted analogs (the 2.1.1.2 and 2.2 analogs, respectively) and oligomers and polymers of the foregoing, as well as various byproducts, especially glutarates. Consequently, though yields were presumably higher than achieved by other methods, purity was not as high as hoped and, as found through subsequent effort, repeatability was erratic at best.

While these advances in the art promoted somewhat higher yields and greater versatility, particularly with respect to the broader variety methylidene malonates, lingering problems persisted, namely batch-to-batch inconsistency, if not outright failure, and the general instability of the subsequent isolation and purification efforts and, for those products that survived, the instability of the so-formed products, especially in bulk storage, and of formulated products, such as adhesives, made with the same.

Due to the inherent problems with instability of the isolation and purification processes, focus instead seemed to focus on efforts to stabilize whatever products were recovered as well as formulated products containing those recovered monomers. For example, Ponticello and Ponticello et. al. suggested that the resulting products could be better stabilized by the addition of certain acidic polymerization inhibitors such as sulfur dioxide, hydrogen fluoride, boron trifluoride, nitric oxide, organic acids, organic anhydrides, stannic chloride and ferric chloride or certain free radical inhibitors such as hydroquinone, catechol, and monomethyl ether of hydroquinone. Although the aforementioned Bru-Magniez et. al. patents did not discuss the inclusion of polymerization inhibitors in their isolated monomer, a review of their subsequent patents demonstrating the utilization of the so formed methylidene malonates made clear that they too employed $SO_2$ as a polymerization inhibitor of the formed methylidene malonates: a fact subsequently confirmed in personal conversations with the successors to the Bru-Magniez technology. For example, Bru-Magniez et. al. (U.S. Pat. Nos. 6,640,461; 6,610,078; and 6,750,298) all speak of the need to degas the monomer under vacuum to remove the polymerization inhibitor $SO_2$. Malofsky et. al. (U.S. Pat. No. 6,512,023) theorized that the stability of 1,1-disubstittuted ethylene monomer and polymers could be improved by the use of specific combinations of certain vapor phase and certain liquid phase anionic polymerization inhibitors. While methylidene malonates fall within that broad class of materials, Malofsky et. al. only demonstrated and, in the prosecution of their patent, argued specificity and uniqueness of their solution to cyanoacrylate monomers and monomer compositions, distinguishing over efforts to stabilize the production of the monomers as well as other monomers.

While Bru-Magniez et. al. certainly achieved many benefits and made significant advances in the production of methylidene malonates and while the addition of the high levels of $SO_2$ polymerization inhibitor to the isolated methylidene malonates and products containing them led to improved bulk storage stability and overall formulated product stability, freezer storage was still required, or strongly recommended, and Bru-Magniez' enthusiasm and accolades relative to industrial scale production were soon found to be tempered by continued inconsistency and instability in production as well as yields that, while higher, were still commercially undesirable, if not unviable. For example, Regula et. al., (U.S. Pat. No. 5,550,172), seemingly in endeavoring to follow the teachings of Bru-Magniez et. al., were only able to attain yields of less than 60 percent based on the adduct, though of high purity. Similarly, our own efforts to duplicate the results attained by Bru-Magniez et. al., even on a bench scale, resulted in wide variation in yields with very few attempts achieving or even coming close to those recited in Bru-Magniez. Indeed, on many occasions our efforts failed altogether due to the in-situ polymerization of the reaction mix in the reactor vessel.

Additionally, these advanced processes continued to require the presence of a suitable solvent, diluent and/or liquid medium, collectively hereinafter the "diluent", in the stripping step, i.e., in stripping the methylidene malonate from the malonate adduct, or the use of high-temperature pyrolysis to recover the methylidene malonate from the malonate adduct. Besides the additional costs of the diluent, their use and disposal introduces further costs and environmental concerns to the overall process. For example, the use of such diluents introduces the need for additional equipment and apparatus for storage, integration and, oftentimes, to enable safe use of the diluents. Additionally, the use of diluents necessarily introduces more steps, and hence time and costs, to the production process, particularly in terms of the separation of the solvents and the removal of solvent from the desired product. Furthermore, these diluents may introduce additional impurities to the reaction mix which, depending upon the recovery process, may lead to the presence of such impurities, or the fractions of the diluents themselves, in the final methylidene malonate product. Without even considering the costs and other factors above, with the ever-growing pressure for "green" processing and manufacture, the elimination of solvents would be of tremendous benefit to commercial producers.

In U.S. provisional patent application, U.S. 61/215,610, filed May 7, 2009, whose filing priority is claimed in the instant application, it was found that marked improvement in stability and yields was attained by use of certain stabilizer systems in the stripping and purification steps of methylidene malonate formation and recovery. However, these processes also employ diluents.

While high temperature pyrolysis is typically a solvent free stripping process, it too has its own issues. Specifically, the high temperatures of pyrolysis may not be suitable for or may adversely affect the specific adducts employed and the intended methylidene malonate end-products. Furthermore, high-temperature pyrolysis adds further energy costs and equipment requirements to the overall process, not just to achieve and control the high pyrolysis temperatures, but also for cooling the associated apparatus and resultant materials as well. In this regard, high-temperature pyrolysis requires specific, costly equipment and apparatus as well as adds time to the overall process as compared to lower temperature methods and methods not temperature reliant.

Despite all of the advances made in the art and the apparent desirability for these materials, the art is still reliant upon the use of diluents and/or high-temperature pyrolysis to strip the desired methylidene malonates from the malonate adducts. Furthermore, the art has yet to adequately address the underlying and critical problems of instability and inconsistency in the production of the methylidene malonates, prior to recovery and distillation. Consequently, the commercial value and opportunity for these products continues to be compromised and overshadowed by the erratic nature of the production process and the attendant costs associated therewith.

Thus, for these products to realize commercial acceptance and utility and for the attributes thereof to be available to the industrial, health and consumer sectors, there remains an urgent need for an environmentally sensitive, cost-effective, viable commercial scale process for the production of methylidene malonates. In particular, there is a need and desire for such a process which avoids the need for diluents and/or pyrolysis in the stripping or recovery step.

Additionally, there remains a need in the industry for a more cost efficient and environmentally acceptable process which avoids or has reduced concern for in-situ polymerization or set-up of the methylidene malonate, particularly as compared to other conventional processes, including diluent-based processes. Specifically, there is also a need for processes that are not fraught with process failures, widely varying yields, unstable products, and unintended polymerizations and other by-products.

Furthermore, there remains a need in the industry for improved processes for the production of methylidene malonates wherein the formation of byproducts, such as glutarates, and dimers, oligomers and polymers of the methylidene malonates as well as thermal degradation products of the foregoing and the starting reactants, are lessened, if not avoided, particularly during the separation and fractionation steps for the recovery of the methylidene malonates.

In particular there is a need for a process that consistently achieves crude yields in excess of 35%, preferably in excess of 45%, more preferably in excess of 50%, especially with purities of the desired product and its analogs on the order of 80%, preferably 90% or more. Indeed, it would be phenomenal to attain purified yields on the order of 30% or more, let alone 40% or more, wherein the resultant product contained less than 8%, preferably less than 6%, most preferably less than 4%, of impurities and less than 12%, preferably less than 10%, most preferably less than 8% of the analogs of the desired product, on a consistent basis, and most preferably without the use of an intermediate adduct.

Indeed, such products would realize their true capabilities if one could produce the same on a commercial scale at a cost comparable to that for the production of cyanoacrylate monomer, in terms of actual costs, yields and/or purity.

Similarly, and in following therewith, there is a ongoing need for methylidene malonates whose bulk and long term storage stabilization is attained without concern for, or certainly less concern with respect to, the impact of such stabilization on the subsequent polymerization characteristics of the so formed methylidene malonates and which can be stored at room temperature. In particular, there remains a need and desire for methylidene malonates that do not require low temperature storage and/or further processing, such as degassing or the addition of scavengers, to remove stabilizers and polymerization inhibitors before the methylidene malonates can be formulated into end-use products and/or used in their intended end-use applications.

Finally, there is a need and desire for methylidene malonates that do not require, or require less, catalyst, polymerization activator and/or accelerator and the like, than heretofore required, in order to attain a sufficient degree and/or speed of polymerization, especially in adhesive and like bonding applications.

SUMMARY OF THE INVENTION

In accordance with the teachings of the present invention there is provided an improved malonate adduct based process for the production of methylidene malonates which process does not rely upon high-temperature pyrolysis or the use of diluents in the stripping step. Specifically, in the production of methylidene malonates wherein elevated temperatures and a stripping agent, typically maleic anhydride, are employed to strip the methylidene malonate from the malonate adduct, it has now been found that one may avoid the use of diluents in the stripping step by instead elevating the temperature of the mixture of the malonate adduct and the stripping agent to or above the temperature at which at least one reactant, and preferably both reactants, melt and maintaining said temperature for a sufficient period of time to allow the stripping reaction to come to completion. Where only one reactant melts, it is preferred that the other is at least partially soluble, preferably substantially, if not fully, soluble in the melt of the other. Typically, the temperature is elevated to no more than 20° C., preferably no more than 10° C., above that temperature at which the one or, as appropriate, both reactants are melted.

The foregoing improved process may, and preferably does, further comprise the addition of one or more reaction phase polymerization inhibitors to the reaction mix containing the intermediate malonate adduct prior to or concurrent with the stripping step and/or one or more separation phase polymerization inhibitors to the methylidene malonate crude product or partially purified product prior to or concurrent with those steps employed to separate and/or isolate the methylidene malonate, as well as to the separated or collected products. Preferably, both the reaction phase and separation phase stabilizers are used. Both of these stabilization steps has been found to greatly reduce, if not eliminate, the instability of these processes and their resultant products, enabling more consistent and predictable processes with high yields of methylidene malonates. In its most preferred embodiment, the one or more polymerization inhibitors, whether reaction phase or separation phase, comprise at least one anionic polymerization inhibitor in combination with one or more free radical polymerization inhibitor.

According to one aspect of the present invention the improved process comprises a two-step process in which a malonic acid ester is reacted with formaldehyde or a formaldehyde source in the presence of a diene or suitable polynuclear aromatic compound or platform to form the associated malonate adduct and the adduct, which, in the second step, is then subjected to a stripping step in which the methylidene malonate is stripped from the platform, wherein the improvement comprises heating the reaction mix containing the malonate adduct and stripping agent, in the absence of a diluent, to a temperature at or above that at which at least one, and preferably both the adduct and agent melt, and maintaining the reaction mix at an elevated temperature throughout the stripping process to maintain the reactant in the liquid state. Preferably, this process further comprises the addition of one or more reaction phase polymerization inhibitors to the formed malonate adduct concurrent with or prior to the stripping step. An especially preferred embodiment is that wherein the platform is cyclopentadiene or anthracene and, if present, the one or more reaction phase polymerization inhibitors comprises at least one primary anionic polymerization inhibitor in combination with one or more free radical polymerization inhibitor.

According to another aspect of the present invention the improved process comprises a one-step process in which a preformed malonate adduct, especially one based on a diene or polynuclear aromatic platform, is subjected to a stripping step in which the methylidene malonate is stripped from the adduct platform wherein the improvement comprises heating the reaction mix containing the malonate adduct and stripping agent, in the absence of a diluent, to a temperature at or above that at which at least one, and preferably both the adduct and agent melt, and maintaining the reaction mix at an elevated temperature throughout the stripping process to maintain the reactant in the liquid state. Preferably, this process further comprises the addition of one or more reaction phase polymerization inhibitors to the formed malonate adduct concurrent with or prior to the stripping step. An especially preferred embodiment is that wherein the platform is cyclopentadiene or anthracene and, if present, the one or more reaction phase polymerization inhibitors comprises at least one primary anionic polymerization inhibitor in combination with one or more free radical polymerization inhibitor.

In accordance with the foregoing embodiments, it is to be appreciated that each process may include additional steps wherein the malonate adduct or malonate precursor thereto is subjected to one or more reactions by which one or both of the ester groups of the "malonate" portion of the adduct or precursor is removed, replaced, or modified. For example, one or both ester groups could be replaced with a higher carbon number hydrocarbyl group, with a hydrocarbyl group different from the other, with a reactive or functional heteroatom or heteroatom-containing radical and the like. With respect to the latter one or both ester groups could be modified or replaced to include an ether, ester, aldehyde, ketone, cyano, aryl, halo or epoxide group.

Furthermore, it is to be appreciated that one may add or, if already used in the stripping process, add additional reaction phase stabilizer, or as discussed below, a separation phase stabilizer, to the reaction product of either of the foregoing processes should the crude product or the isolated crude liquid product be stored before further efforts are undertaken to isolate and purify the methylidene malonate. In this regard, it is understood that the crude product of the foregoing processes will be subjected to one or more separation and/or purification steps or processes, most preferably by separation and/or crude distillation followed by a plurality of fractionation or distillation steps, depending upon the purity attained and/or desired or needed.

Thus, according to a third aspect of the present invention there is provided an improved process for the production and recovery of methylidene malonates, from a malonate adduct (or a malonic acid ester or malonate precursor in the case of the two-step process) to a purified methylidene malonate, wherein the improvement comprises conducting the stripping step whereby the methylidene malonate is stripped from the malonate adduct without pyrolysis and in the absence of a diluent, wherein said process is conducted at a temperature at or above that at which at least one, and preferably both, of the malonate adduct and stripping agent melt, and maintaining the reaction mix at an elevated temperature throughout the stripping process to maintain the reactant in the liquid state, generally at or near the same temperature. Preferably, this process further comprises the addition of a reaction phase polymerization inhibitor system to the adduct prior to or concurrent with the stripping step and/or the addition of a separation phase polymerization inhibitor system to the crude reaction product and partially purified products to be further purified prior to or concurrent with the separation, purification, and recovery phase of the methylidene malonate production process as well as to the final methylidene malonate recovered, or both.

Where present, the separation phase polymerization inhibitor may be the same as the reaction phase polymerization inhibitor or a different polymerization inhibitor system comprising components suitable for use as reaction phase polymerization inhibitors or it may comprise at least one secondary anionic polymerization inhibitor, alone or in combination with one or more free radical polymerization inhibitors. As with the reaction phase polymerization inhibitor, the separation phase polymerization inhibitor system preferably comprises at least one liquid phase anionic polymerization inhibitor alone or, more preferably, in combination with one or more free radical polymerization inhibitors.

While the separation phase polymerization inhibitor is added to the crude or partially purified materials to be further purified, the same or a different separation phase polymerization inhibitor may also be, and is preferably, added to the collected material arising from each separation or fractionation process following its collection. Most preferably, a portion of the latter separation phase polymerization inhibitor is to be added to the collection flask or vessel prior to initiation of the separation process and the remainder added to the collected material following completion of the collection. The amount of the separation phase polymerization inhibitor system to be added to the empty collection flask or vessel will be based on the theoretical or projected amount of material to be collected (or a substantial portion thereof): generally the amount will be somewhat less than that needed if the full amount projected to be recovered were to actually be recovered. Once the separation is completed, the amount of separation phase polymerization inhibitor is then adjusted upward, as appropriate, based on the actual amount collected. This same process, i.e., the addition of the separation phase polymerization inhibitor system, will be used for each successive separation or purification step employed, if any.

While the present invention has the benefits of simplicity, efficiency, and lower cost as well as the environmental, health and safety benefits due to the absence of the diluent and the use of reactants in the melt phase, the addition of the polymerization inhibitors, as mentioned above, has marked improvements on the overall process. Specifically, by implementing the improved processes as set forth herein, one realizes more consistent and improved yields. For example, one may attain crude yields in excess of 35%, preferably in excess of 45%, more preferably in excess of 50%, most preferably in excess of 60% or more, even 70 or 80% or more, on a consistent and repeatable basis. Most importantly, these yields are attained with a concomitant high purity, generally 60% or more, preferably 75% or more, more preferably 80% or more, most preferably 90% or more.

Furthermore, one may achieve even higher purities, with only minimal or modest loss in yield, but still excellent yields, by the further fractionation of the partially purified products attained by the improved separation processes. Generally, one is able to realize purified yields in excess of 20%, preferably in excess of 30%, more preferably in excess of 35%, most preferably of about 40% or more, based on the theoretical yield possible from the original malonate adduct, on a repeatable and consistent basis. Furthermore, these "purified" fractions or collections of methylidene malonate generally have purities exceeding 80%, preferably 85%, more preferably 90%, most preferably 95%. Thus, even if the yields, especially the purified yields, slip below the aforementioned targets, the loss in yield is more than made up for by the increased purity attained with the improved processes. Hence; yields as low as 15%, even 10%, with high purity of 85% or higher, preferably 90% or higher, most preferably 95% or higher, provides a suitable process and is within the scope of the present invention. Generally speaking, the improved processes of the present invention provide for high purity wherein the purified product contains less than 8%, preferably less than 6%, most preferably less than 4%, of impurities and less than 12%, preferably less than 10%, most preferably less than 8% of the analogs of the desired product, on a consistent basis.

In accordance with another aspect of the present invention there are provided stable, high purity methylidene malonates, in crude and/or purified form, produced by any of the foregoing improved methods wherein a polymerization inhibitor has been employed as noted above. In particular, there are provided stable, high purity methylidene malonates comprising the methylidene malonate and an effective amount of a polymerization inhibitor combination of at least one anionic polymerization inhibitor and one or more free radical polymerization inhibitor.

DETAILED DESCRIPTION

As used herein and in the appended claims, and as already noted above, the term "diluent" is used to refer to a solvent, liquid medium or other diluent traditionally used in the stripping step of methylidene malonate production. Similarly, as used herein the term "crude product" or "crude yield" means that reaction product containing the intended methylidene malonate subsequent to the striping of the methylidene malonate from the adduct and prior to any separation or isolation steps to remove the non-liquid components, e.g., residue of the maleic acid and/or the platform molecule of the adduct. As context allows, it may also mean that liquid reaction product remaining after separation, whether by filtration, crude distillation or the like, of the liquid materials from the solids in the reaction product mix: although this is oftentimes referred to as the crude liquid product. Also, as used herein the term "initial re-distillation" or "second distillation" refers to the initial distillation of the crude yield, i.e., liquid monomer distilled from or otherwise separated from the reaction mix. The term "fractionation" is used herein to mean the act or process of separating, isolating and/or purifying the methylidene malonate from the liquid phase of the crude reaction product, most notably, from the crude liquid reaction product, as well as any subsequent steps or processes to further increase the purity thereof. Further, when referencing the amount of polymerization inhibitors to be used, the amount is presented in parts per million (ppm) based on the weight of the malonate adduct (unless otherwise indicated) in the case of the reaction phase polymerization inhibitors and on the theoretical weight of the recoverable methylidene malonate in the case of the separation phase polymerization inhibitors, unless otherwise indicated. Finally, it is to be noted that the terms "stabilizer" and "polymerization inhibitor" are used interchangeably herein: each having the same intended definition.

Methylidene malonates are compounds having the general structure (I):

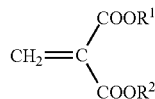

(I)

wherein $R^1$ and $R^2$ may be the same or different and represent H or a $C_1$ to $C_{18}$ hydrocarbon group or heterohydrocarbon group having one or more nitrogen, halogen, or oxygen atoms; provided that $R^1$ and $R^2$ are not both H. Preferably each $R^1$ and $R^2$ are each independently a $C_1$ to $C_{10}$, most preferably a $C_1$ to $C_6$, linear or branched alkyl group; a $C_3$ to $C_6$ alicyclic group; a $C_2$ to $C_6$ alkenyl group; or a $C_2$ to $C_6$ alkynyl group; any of which may optionally be substituted with an ether, epoxide, halo, ester, cyano, aldehyde, ketone or aryl group. A further preferred subset of methylidene malonates are those wherein one or both of $R^1$ and $R^2$, which may be the same or different, are of the formula (IV):

 (IV)

wherein $R^8$ is a $C_1$ to $C_6$ lower alkyl and n is an integer of from 1 to 5, said ester group most preferably having been formed as a result of an ester exchange reaction.

The improved process of the present invention may be adapted to/adopted for use in any of the conventional methods for the production of methylidene malonates involving the formation of or starting with a malonate adduct wherein the desired methylidene malonate is stripped from the malonate adduct, especially a diene or polynuclear aromatic platform, by a suitable stripping agent. Specifically, it has now been found that one may strip methylidene malonates from such adducts without pyrolysis and in the absence of a diluent by heating the reactants to a temperature where at least one of the adduct and/or the stripping agent, preferably both, melt and allowing the stripping process to proceed at an elevated temperature, preferably the same temperature, whereby the reactants remain in a liquid state during the stripping process. Furthermore, one may markedly and surprisingly improve the yield, stability and/or predictability of the improved process by the inclusion of certain polymerization inhibitors prior to or concurrent with the stripping step and/or in the separation, purification and recovery of the desired methylidene malonate.

In accordance with the first embodiment of the present invention, there is provided an improved "two-step process" for the production of the methylidene malonates. The two-step process generally refers to that process in which one first prepares the intermediate malonate adduct, the first step, and then proceeds with the stripping step, the second step. Specifically, the two-step process generally comprises the steps of reacting a malonic acid ester, preferably the diester, with formaldehyde in the presence of a diene or polynuclear aromatic platform to form the malonate adduct and, sequentially or at some later point thereafter, subjecting the so formed or further modified adduct to a stripping process by which the methylidene malonate is stripped from the platform.

As noted, the two-step process typically involves an initial Diels-Alder reaction between a malonic acid ester and formaldehyde or a suitable formaldehyde source in the presence of a suitable conjugated diene or polynuclear aromatic platform. Malonic acid esters are generally of the formula (VI)

(VI)

wherein $R^{11}$ and $R^{12}$ may be the same or different and represent H or a $C_1$ to $C_{18}$, preferably a $C_1$ to $C_{10}$, most preferably a $C_1$ to $C_6$, linear or branched alkyl group; a $C_3$ to $C_6$ alicyclic group; a $C_2$ to $C_6$ alkenyl group; or a $C_2$ to $C_6$ alkynyl group, but $R^{11}$ and $R^{12}$ are not both H. Additionally, either or both of the aforementioned $R^{11}$ and $R^{12}$ groups may be substituted with an ether, epoxide, halo, ester, cyano, aldehyde, ketone or aryl group, especially desirable are those wherein at least one of the $R^{11}$ and $R^{12}$ groups is of the formula (IV):

 (IV)

wherein $R^8$ is a $C_1$ to $C_6$, preferably a $C_1$ to $C_3$, lower alkyl and n is an integer of from 1 to 5, preferably 1 or 2. The acid may be a monoester or a diester, but is preferably a diester. Exemplary malonic acid esters include dimethyl malonate, diethylmalonate, diisopropyl malonate, di-n-propyl malonate, and ethyl methyl malonate as well as those wherein one of $R^{11}$ and $R^{12}$ is $—(CH_2)_n—COOR^8$ wherein $R^8$ is a $C_1$ to $C_3$ lower alkyl and n is 1 or 2.

As used herein the term "formaldehyde" refers to formaldehyde as well as to any source of the compound having the formula H—C(O)—H such as paraformaldehyde, formalin, gaseous formaldehyde and the like.

As used herein the term "diene" refers to conjugated diene platforms. These include the linear conjugated diene compounds corresponding to the following formula:

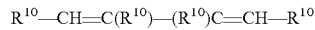

wherein each $R^{10}$ is independently hydrogen, methyl or ethyl as well as the corresponding alicyclic dienes. Suitable dienes include 2-methyl-1,3-pentadiene, 1,3-hexadiene, cyclopentadiene, isoprene, 1,3-butadiene, 2,4-hexadiene, 2,3-dimethyl-1,3-butadiene, etc.

"Polynuclear aromatic compounds" are compounds that have multiple, fused, six-membered rings, all or most of which are aromatic rings, especially those of the benzenoid type. Such compounds are also well known. Preferred polynuclear aromatic platforms include anthracene, naphthalene, naphthacene, and phenanthrene, most especially anthracene.

The reaction conditions as well as other constituents that may be present in the formation of the malonate adducts, including solvents, catalysts, etc. and their amounts, are all well known in the art and will be further discussed below.

Generally speaking, when preparing the malonate adduct, the conjugated diene or polynuclear aromatic platform is typically present in about an equimolar amount to a slight molar excess, preferably from about 1.0× to 1.4×, most preferably a 1.0 to 1.2×, molar excess relative to the malonic acid ester, whereas formaldehyde or the formaldehyde source and malonic acid ester are generally combined in equimolar or near equimolar amounts. The reaction is generally conducted at reflux temperature, e.g., about 50° C. to about 110° C., preferably from about 70° C. to about 90° C., to form the adduct mixture. Water formed by this process may be azeotroped out with the excess diene or aromatic compound.

The initial step, i.e., the reaction of the formaldehyde with the malonic acid in the presence of the platform material, is preferably conducted in a suitable solvent, preferably a non-aqueous solvent, in the presence of a catalyst. Such catalysts are generally present at from 0.1 to about 10 weight percent based on the weight of the malonate ester.

Suitable catalysts include primary, secondary and tertiary amines, especially secondary aliphatic amines; particularly where the platform is a conjugated diene. Exemplary amine catalysts include piperidene, piperazine, N-methylpiperazine, dibutylamine, morpholine, diethylamine, pyridine, triethylamine, tripropylamine, triethylenediamine, N,N-dimethylpiperazine, butylamine, pentylamine, hexylamine, heptylamine, nonylamine, decylamine, and the like. Especially preferred amines include piperidene, piperazine, N-methylpiperazine, dibutylamine, morpholine, and diethylamine. The salts of these amines with organic monocarboxylic acids, such as piperidine acetate, also act as effective catalysts.

Alternatively, where the platform is a polynuclear aromatic compound, the catalyst is preferably a metal salt of a lower monocarboxylic acid such as copper(II) acetate, cupric acetate monohydrate, potassium acetate, zinc acetate, zinc chloracetate, magnesium chloracetate, magnesium acetate, and combinations of any two or more thereof, especially copper(II) acetate, potassium acetate and combinations of the two.

Although non-aqueous solvents are preferred, the reactions may be conducted in either an aqueous or a non-aqueous medium. Advantageously, the non-aqueous medium may be a water miscible solvent, a water immiscible solvent, or a combination of at least one water miscible solvent and at least one water immiscible solvent: the choice being dependent upon the particular system and materials employed. Exemplary non-aqueous solvents include, but are not limited to, acetic acid, acetic anhydride, glacial acetic acid, benzene, bromobenzene, xylene, toluene, dimethylformamide (DMF), dimethylsulfoxide (DMSO), tetrahydrofuran, a ketone such as dimethyl ketone or ethylmethyl ketone, alkanes such as heptane to hexane, acetonitrile, dioxane, N-methylpyrrolidone (NMP) or combinations of any two or more of the foregoing. Exemplary combinations include, but are not limited to glacial acetic acid/xylene, benzene/acetic acid, xylene/acetic acid/acetic anhydride, dimethyl ketone/acetic acid, ethylmethyl ketone/acetic acid, acetonitrile/acetic acid and the like.

The resultant product of this initial step is an intermediate malonate adduct which has the following structure (VII):

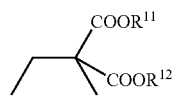
(VII)

incorporated into or bonded to the platform species, most often incorporated into a ring structure with the diene or as a pendant ring to the pre-existing ring structure of an alicyclic diene or polynuclear aromatic compound. For example, when the conjugated diene is a linear conjugated diene, the malonate adduct will have a single ring structure with the above structure (IV) forming part of that ring. On the other hand, when the conjugated diene is cyclopentadiene or the polynuclear aromatic compound anthracene the structure (IV) forms a pendant ring to the existing rings, e.g., the former results in a norbornene ring structure. Such intermediate malonate adducts and their formation are disclosed in the aforementioned Hawkins et. al., Ponticello, Ponticello et. al. and Bru-Magniez patents.

The resultant reaction mix comprising the malonate adduct is then subjected to such processes as appropriate, and as known in the art, to separate and recover the solid malonate adduct. For example, any catalysts employed in the adduct formation or in any other subsequent reactions involving the initial adduct, e.g., in any transesterification reaction, hemihydrolysis, etc., prior to the stripping step, will be extracted from the reaction product before stripping. Similarly, depending upon the solvents used in those processes, suitable steps are to be employed to remove the solvent and/or isolate/precipitate out the solid adduct.

Once the adduct is isolated, the adduct is then subjected to a stripping process to recover the methylidene malonate or it may first be subjected to any number of alternative processes for removing and/or altering the ester groups, as mentioned above. For example, again as mentioned above, the formed malonate adduct may be subjected to hemihydrolysis and subsequent alkylation to form an asymmetrical malonate adduct. Other processes and reactions for forming other malonate adducts having symmetrical or asymmetrical ester groups, higher carbon number ester groups and/or hetero atom containing ester groups are all known in the art.

The second step of the two-step process, which is also the key step of the one-step process, comprises the stripping of the methylidene malonate from the intermediate malonate adduct or, in the case of the "one-step process," a preformed malonate adduct. Where a preformed malonate adduct is employed, the malonate adduct may have been made by any of the methods known in the art, including, but not limited to, the two-step process mentioned above, as well as by similar reactions in which, for example, alkyl acrylates are reacted with a diene or polynuclear aromatic platform, as disclosed in Ponticello et. al. The formation of such malonate adducts is well know, as are the reaction conditions and other co-constituents such as catalysts, solvents and the like. Furthermore, certain of these malonate adducts are commercially available from Virsol of Paris, France.

Many methods are well known for recovering or, more appropriately, stripping the methylidene malonate from the malonate adduct. Several of these have extreme condition requirements, e.g., pyrolysis and the like. The most traditional stripping methods involve the use of heat and a suitable stripping agent, namely an agent known in the art suitable for reversing the Diels-Alder reaction, especially maleic anhydride, in the presence of an appropriate diluent. Exemplary diluents include paraffin oil, mineral oil, tricresyl phosphate, and the like.

Surprisingly, it has now been found that stripping of the methylidene malonate may be accomplished in the absence of a diluent and without pyrolysis. Specifically, in accordance with the practice of the present teachings, it has now been found that methylidene malonates may be recovered from the malonate adduct by heating the same, in the presence of the appropriate stripping agent, but without a diluent, to a temperature at or above temperature that at which at least one and preferably both of these components melt and conducting the stripping process at that temperature or a similar temperature whereby the reactants are maintained in a liquid state.

When maleic anhydride or another suitable stripping agent is employed, it is present in at least a near equimolar, preferably an equimolar amount, to a molar excess amount based on the moles of adduct or intermediate adduct. Generally, the amount of maleic anhydride or other suitable stripping agent will be from about 0.8× to about 2×, preferably from about 1× to 1.5×, most preferably >1× to 1.3×, the number of moles of adduct or adduct intermediate. Higher or lower amounts could also be used; but higher amounts will just add cost and waste whereas lower amount will result in reduced yields and/or slower reactions.

As noted above, the temperature to be employed is at least that at which both the stripping agent and the malonate adduct melts. Somewhat higher temperatures are beneficial; however, consistent with the desire to be as cost effective as possible, the temperature to which the mixture is raised need be no more than about 20° C., preferably no more than about 10° C., higher than the melt temperature of the mixture. Higher temperatures could be used, but such is not necessary. In any event, one would not heat, nor desire to heat, the mixture to a temperature at which true pyrolysis of the adduct and/or stripping agent takes place. Thus, it is likely that anything more than about 50° C. above the melt temperature would be inappropriate or, in any event, unnecessary.

Besides the obvious environmental, health and safety benefits attained by being able to avoid the use of the diluent, as well as the reduced costs associated with not having to use a diluent and to worry about solvent recovery and containment equipment and the like, there is another unexpected benefit owing to the large volume difference between the solid adduct and the liquid adduct. Specifically, and this is especially noted for batch reactions, one is able to put a much larger amount of adduct in a given vessel in its liquid state than in its solid state. Thus, much larger quantities of adduct can be stripped in a given batch.

In all of the aforementioned processes, it is to be appreciated and understood that the number of steps recited, namely the "two-step process" or the "one-step process" refers only to the adduct formation and stripping steps. Typically the production of methylidene malonates can, and most preferably does, involve other process steps for the production and/or isolation of the ultimately desired methylidene malonate compounds.

In this regard, it is to be appreciated that improved processes for the production of the methylidene malonates according to the present invention may further comprise any number of additional steps whereby the malonate adduct, in either process, or, in the case of the two-step process, the malonate precursor is subjected to one or more additional reactions by which one or both of the ester groups of the malonate or precursor is removed, replaced, and/or modified. Such reactions enable one to tailor the final structure and functionality of the methylidene malonate to be produced. For example, such processes allow one to substitute one or both ester groups with different hydrocarbyl groups, typically higher carbon number hydrocarbyl groups: the former enabling the production of asymmetrical methylidene malonates and the latter most preferably producing methylidene malonates of higher carbon number. Similarly, such reactions may be employed to modify or substitute one or both ester groups with an ester group incorporating any number of reactive or functional groups or radicals or with an alternate reactive or functional group altogether. For example, the ester may be modified or substituted with or replaced by a further reactive or functional group or a non-functional group, including, e.g., an ether, epoxide, halo, ester, cyano, aldehyde, ketone or aryl group. Further, such groups or moieties could be functional or reactive groups or moieties for subsequent cross-linking and/or co-polymerization of the methylidene malonates with itself or, preferably, with other monomers, compounds, reactants, cross-linkers, hardeners, etc.

Suitable methods for accomplishing the foregoing are well known. For example, monoesters can be prepared from the dialkyl adducts by reacting the same with an alkali metal or alkaline earth metal salt, especially sodium or potassium hydroxide, in an alcoholic solvent. Similarly, asymmetric compounds may readily be prepared from the monoester addition product by reaction with a halogen-containing product whose radical is to form a second ester radical which is different from the first ester radical. Transesterification is an especially desirable method by which such asymmetrical or heteroatom-containing compounds are formed. Such processes are described in, for example, Hawkins et. al. (U.S. Pat. No. 4,049,698), Ponticello (U.S. Pat. No. 4,056,543), Ponticello et. al. (U.S. Pat. No. 4,160,864), and Bru-Magniez et. al. (U.S. Pat. Nos. 4,932,584 and 5,142,098), all of which are hereby incorporated herein in their entirety by reference.

Thus, in its broadest concept, the present invention relates to an improvement in those processes for the production of methylidene malonates wherein the latter are stripped from a malonate adduct or like intermediate based on a conjugated diene or polynuclear aromatic platform wherein the improvement lies in the step of heating the malonate adduct and stripping agent to a temperature at or above that at which the aforesaid mixture melts and holding the melted mixture at that temperature for a sufficient period of time to complete the stripping reaction, all without the need or use of traditional diluents or the like, e.g. mineral oil, paraffin oil, tricresyl phosphate, etc., for the stripping step. Most commonly, such stripping is achieved by heating the malonate adduct in the presence of a compound that, under the melt conditions mentioned above, facilitates the stripping of the methylidene malonate from the adduct. It is believed, though not confirmed, that the stripping agent, under the elevated temperature conditions, substitutes for the methylidene malonate on the conjugated diene or polynuclear aromatic platform, e.g., maleic anhydride.

Although the foregoing discussion contemplates that the adduct and stripping agent are elevated to a temperature above which both have melted, it is understood that reference to the melting of the adduct and the stripping agent as used herein and the appended claims is also to be understood to include those situations where one may have melted and the other is soluble or at least partially soluble or, if already a liquid, miscible or partly miscible in the other.

Surprisingly, it has also been found that the improved process of the present invention may be, and preferably is, further improved and enhanced by the addition of certain polymerization inhibitors to the stripping and/or subsequent separation and/or purification processes. Such modified processes are described in U.S. provisional patent application Nos. 61/215,610 and 61/215,578, both of which were filed on May 7, 2009, and 61/291,898, which was filed on Jan. 1, 2010, as well as in co-filed U.S. non-provisional patent application Ser. No. 12/774,810 (now Patent Application Publication No. 2010/0286438 A1) entitled Improved Methylidene Malonate Process which claims the priority thereof, all of which are incorporated herein by reference in their entirety.

Specifically, it has now been found that one may markedly improve the stability of the stripping process, the storage stability of the resulting crude products, the stability of any subsequent separation and purification steps of the crude product or any partially purified products, as well as the purified and partially purified products themselves by the use of certain polymerization inhibitors, specifically by the use of a combination of inhibitors, namely at least one anionic polymerization inhibitor and one or more free radical polymerization inhibitors. The presence of these inhibitors prevents or at least markedly reduces any reversion of the stripping process and/or polymerization of the methylidene malonate monomers, without interfering with the stripping process itself and/or the purification processes.

To stabilize the stripping process, a reaction phase polymerization inhibitor is combined with the adduct prior to or concurrent with the stripping process. In the case of a two-step process, the reaction phase stabilizer is added following the isolation and recovery of the adduct and prior to initiating the stripping reaction. The reaction phase polymerization inhibitor may be added in its neat form or it may be added as a concentrate in a minor amount of a solvent or co-reactant: the amount of the solvent or co-reactant being insignificant such that the stripping reaction is still considered solvent free or in the absence of a solvent or diluent.

Where the crude product of the stripping process is to be stored, additional reaction phase polymerization inhibitor or a separation phase polymerization inhibitor is added thereto. On the other hand, if the crude reaction product is to be subject to one or methods by which the liquid phase of the reaction product, i.e., that phase containing all or the bulk of the methylidene malonate, is separated from the other components, e.g., the spent platform compound or derivative, the added polymerization inhibitor is best added after isolation of the crude liquid product. At this point, the polymerization inhibitor may be either the same or a different reaction phase polymerization inhibitor or a separation phase polymerization inhibitor.

Having stripped the methylidene malonate from the adduct and having separated the crude liquid methylidene malonate containing component from the other components of the reaction mix of the stripping process, one may also further improve the process of the present invention by performing one or more, preferably a plurality of, purification processes to separate and purify the methylidene malonate product. Most preferably, in according with yet another aspect of the present invention, the separation, purification and recovery of the methylidene malonate is carried out in the presence of a separation phase polymerization inhibitor, which, as to be noted in further detail below, is also to be added to each collected fraction of the methylidene malonate. Generally speaking, the products of the stripping process will undergo a plurality of sequential separation and/or distillation steps to isolate the stripped materials from the adduct platform and any solvent or reaction medium as well as to further purify each collected fraction or product of the purification step(s).

Like the reaction phase stabilizer system employed in the stripping process, the separation phase stabilizer system comprises one or more anionic polymerization inhibitors, at least one of which must be a liquid phase anionic polymerization inhibitor, alone or in combination with at least one free radical polymerization inhibitor. However, unlike the reaction phase stabilizer system, the anionic polymerization inhibitor(s) of the separation phase stabilizer system may be primary anionic polymerization inhibitors or secondary anionic polymerization inhibitors, or a combination thereof. Additionally, in those situations where the fractionation process is merely a continuation of the reaction process discussed above (i.e., the two-step process), one may optionally employ the reaction phase stabilizer system as the separation phase stabilizer system, at least for stabilization of the crude product or, if separated, the crude liquid product. Generally, though, the reaction phase stabilizer system and the separation phase stabilizer system will be different, especially in the collected materials from each aspect of the purification process. Specifically, while the separation phase stabilizer for the crude product, or the isolated liquid product, resulting from the one-step or two-step process may be the same as the reaction phase stabilizer, the separation phase stabilizer to be added to each fraction or mass of material collected from the separation process will typically be different, most especially in the case of the finally purified material.

The improved separation process of the present invention may be applied to any of the known processes for the fractionation or separation, purification and recovery of methylidene malonates. Such methodologies include: distillation (including fractional distillation), flash distillation, solvent stripping, crystallization, precipitation, extraction, gel filtration, electrophoresis, foam fractionation, electromagnetic separation, evaporation (including thin film evaporation), press extraction, and various forms of chromatography as well as combinations of the foregoing. For convenience, the following discussion will be made with respect to distillation, notably fractional distillation; though it is to be appreciated that those skilled in the art will readily appreciate the modifications and variations that will be needed to adopt the process to the other fractionation methods.

Although it is preferred that a reaction phase polymerization inhibitor be used in combination with the inventive, solvent free stripping process of the present invention, if not, then the crude product thereof, especially the crude liquid product, should be stabilized with a separation phase polymerization inhibitor before commencing fractionation. This separation phase stabilizer system may be the same or different from the separation phase stabilizer system to be added to the recovered fractions. Similarly, even if the crude product to be subjected to fractionation contained an alternate stabilizer or stabilizer system or a reaction phase polymerization inhibitor, one may consider supplementing, and preferably will supplement, the stabilization of the crude product with an amount of the separation phase stabilizer system.

While the separation phase stabilizer system may be added to the recovered material during or following its collection, it is preferred that at least a portion of the separation phase stabilizer system be added to the collection flask or vessel prior to initiating fractionation or at least prior to collection of the fraction to be recovered and the remainder added following completion of the fractionation or, as appropriate, collection of the given fraction(s). The amount of the separation phase stabilizer system to be added to the empty collection flask or vessel will be based on the projected amount of material to be collected: generally the amount will be somewhat less than that needed if the full amount projected were to actually be recovered. Once the fractionation is completed, the level of separation phase stabilizer will then be adjusted upward, as appropriate, based on the actual amount collected. And, as with the reaction phase stabilizer system, it is preferred, though not required, that all components of the separation phase stabilizer system be added concurrently or nearly so. The exception, of course, is where a vapor phase stabilizer is to be continuously introduced to the fractionation apparatus, as further described below.

The process as described above, i.e., the addition of the separation phase stabilizer system, will be used for each successive fractionation process and/or fractionation step employed. For example, in fractional distillation, if a given fraction or combination of fractions is to be redistilled, the fractions collected during the re-distillation will also be stabilized with the separation phase stabilizer and the materials to be fractionated will be up-stabilized, as appropriate. Additionally, it is to be appreciated that a given process may involve different separation phase stabilizers during the full course of the separation, purification and recovery steps. For example, while one separation phase stabilizer system may be employed for each distillation step or a multi-step distillation, a different separation phase stabilizer may be used in the final, purified products (and hence its collection vessel if pretreated).

In the practice of the preferred embodiment of this aspect of the present invention, i.e., that where the solvent free stripping is combined with the stabilized separation, purification and recovery process, it is most convenient to place a quantity of a stock solution of the separation phase stabilizer system, or one or more components thereof, especially, the anionic polymerization, in the collection vessel or container, allow the solution to evenly coat the inner surface of the collection vessel or container and then pour out the excess. Since the solvent for the stock solution is typically a volatile solvent, e.g., toluene, ethanol, acetone, etc., or a copolymerizable or inert monomer, e.g., an acetate or acrylate, the container or vessel is promptly attached to the fractionation apparatus or sealed to prevent loss of the stabilizer solution until the container or vessel is to be attached to the fractionation apparatus. On the other hand, so long as the loss of solvent will not affect the inhibitors in the vessel, which essentially coat the inside wall of the vessel, one may allow some or all of the solvent to evaporate before sealing to protect the remaining inhibitors. One can calculate the amount of inhibitor(s) left in the container or vessel by weighing the weight gain. Then, once the separation process is completed and the collected sample sealed in the container, the container is then again weighed and the proper weight of the recovered material determined so that one can then determine the amount of stabilizer to be added to bring the total stabilizer content to the appropriate level.

Depending upon the nature of the fractionation process employed, it is preferred to include one or more vapor phase or dual liquid-vapor phase anionic polymerization inhibitors in the separation phase stabilizer system. This is particularly so for those fractionation processes which involve the formation of a vapor of or containing the methylidene malonate. If the system is a closed or sealed system, then one only need add the vapor phase stabilizer with the liquid phase stabilizer. However, if it is an open system or a system under a drawn vacuum, then it is necessary to supply a continuous feed of the vapor phase stabilizer to maintain a given level of the stabilizer in the vapor phase or the airspace of the apparatus. For example, in a traditional distillation apparatus, especially one that is under vacuum, it is preferred to bubble a constant vapor of the vapor or dual liquid-vapor phase polymerization inhibitor through the system.

The adoption of either or both of the improved reaction and separation processes described above results in a marked stability to the overall process, thereby enabling consistent and more predictable results. In addition to the enhanced stability and, hence, predictability achieved by the use of the stabilizer systems, their use also results in still higher yields of greater purity, particularly as compared to the performance of similar processes conducted in the absence of polymerization inhibitors or with other stabilizers.

Specifically, by implementing the preferred embodiment of the present invention, namely the solvent free stripping and the reaction phase and separation phase polymerization inhibitors, as set forth herein, one realizes more consistent and improved yields. For example, one may attain crude yields in excess of 35%, preferably in excess of 45%, more preferably in excess of 60%. In those situations where the improved separation process of the present invention is applied to non-adduct processes, as mentioned above, one may attain yields in excess of 25%, preferably in excess of 35%, more preferably in excess of 40%, most preferably in excess of 50% or more, on a consistent and repeatable basis. This is surprising in light of the prior art teachings as set forth in the Background. Regardless, of particular importance is the fact that these yields are attained with a concomitant high purity, generally 60% or more, preferably 75% or more, more preferably 80% or more, most preferably 90% or more, with or without the use of the intermediate adducts. More importantly, the further fractionation of these yields by the improved separation process and associated separation phase stabilizer system results in even higher purities with excellent yields. Generally, one is able to realize purified yields in excess of 20%, preferably in excess of 30%, more preferably in excess of 35%, most preferably of about 40% or more, based on the original malonate reactant, on a repeatable and consistent basis. Furthermore, these "purified" fractions or collections of methylidene malonate generally have purities exceeding 80%, preferably 85%, more preferably 90%, most preferably 95%. Thus, even if the yields, especially the purified yields, slip below the aforementioned targets, the loss in yield is more than made up for by the increased purity attained with the improved processes. Hence; yields as low as 15%, even 10%, with high purity of 85% or higher, preferably 90% or higher, most preferably 95% or higher, provides a suitable process and is within the scope of the present invention. Generally speaking, the improved processes of the present invention provide for high purity wherein the purified product contains less than 8%, preferably less than 6%, most preferably less than 4%, of impurities and less than 12%, preferably less than 10%, most preferably less than 8% of the analogs of the desired product, on a consistent basis.

Thus, while there may be, and most likely is, some loss in overall yield as a result of the fractionation process, especially if multiple fractionation processes are employed or the same process is repeated one or more times, the purity of the product significantly improves. This is especially important from a commercial perspective as the purity of the methylidene malonate is critical to and correlates with its utility and performance. Specifically, as discussed in Coover et. al. (U.S. Pat. No. 3,221,745) and as found by Applicants, even minor amounts of impurities impair their utility, especially the cure or polymerization characteristics of these monomers. Concern with the presence and amount of impurities and byproducts is even more paramount, if not an absolute use limiting factor, in the case of methylidene malonates intended for medical applications, especially skin bonding applications, e.g., skin bonding adhesives, or other applications that may require its use in the human body.

Suitable reaction phase polymerization inhibitors comprise at least one anionic polymerization inhibitor (also referred to as the primary anionic polymerization inhibitor), at least one of which is a liquid phase anionic polymerization inhibitor, alone or in combination with at least one inhibitor of free radical polymerization. Preferably the primary anionic polymerization inhibitor(s) is an acid, especially a mineral acid, an organic acid, or a sulfonic acid. Especially suitable anionic polymerization inhibitors are characterized as being strong acids, most preferably very strong acids. As used herein, a strong acid is an acid that has an aqueous pKa at room temperature of about 2.0 or less and a very strong acid is one having an aqueous pKa of about 1.0 or less. Strong acids include, but are not limited to, strong mineral acids and strong organic acids including maleic acid, difluoroacetic acid, dichloroacetic acid, and picric acid. The very strong acids include, but are not limited to, the very strong mineral and/or oxygenated acids as well as the sulfonic acids. By way of example, but not limitation, exemplary very strong acids include sulfuric acid, nitric acid, perchloric acid, trifluoroacetic acid, trichloroacetic acid, hydrochloric acid, hydrobromic acid, benzene sulfonic acid, methane sulfonic acid, trifluoromethane sulfonic acid, fluorosulfonic acid, chlorosulfonic acid, paratoluene sulfonic acid, and the like. Preferably the primary anionic polymerization inhibitor is selected from trifluoroacetic acid, sulfuric acid, maleic acid, perchloric acid and chlorosulfonic acid; most preferably sulfuric acid, maleic acid, and/or trifluoroacetic acid. In part, the selection of the stabilizer is temperature dependent. For example, high temperature adduct processes favored the use of maleic acid as the reaction phase stabilizer over sulfuric acid. The latter, though, appears to be preferred over the maleic acid when adding it to the isolated product.

With certain exceptions, it is preferred that the individual polymerization inhibitors making up the reaction phase stabilizer system are not readily vaporized or otherwise drawn or removed from the crude product or crude liquid product, as appropriate, on standing or under the selected fractionation technique to be employed for the separation and recovery of the purified methylidene malonate. This is especially important in high temperature separation steps such as distillation, particularly fractional distillation. While the passing over of small amounts of the anionic polymerization inhibitor may be tolerated and acceptable, it is generally preferred that no or negligible amounts pass over so as to avoid the happenstance that the crude reaction product becomes deficient in the amount of stabilizer present before separation is completed. A deficiency in the level of the stabilizers will lead to a general instability of the reaction product which, in turn can lead to an undesirable and untimely formation of oligomers and/or polymers of the methylidene malonate and/or the formation of other byproducts and degradation products, especially glutarates: all of which will reduce significantly the yield of recovered material in the collection vessel.

The first exception is where the anionic stabilizer is employed in a sufficient excess to account for the loss or passing over of the stabilizer in the vapor phase.

The second exception to the foregoing is polymerization inhibitors that distill over slowly so as to remain in sufficient quantities in the crude reaction product or crude liquid reaction product so as to prevent its premature polymerization prior to completion or substantial completion of the separation process. These inhibitors have the added benefit of serving as a stabilizer of the vapor phase as it traverses to the collection flask. Thus, for the purpose of this application and the appended claims, dual functional liquid-vapor phase anionic polymerization inhibitors are to be deemed liquid phase anionic polymerization inhibitors: thereby satisfying the need for the at least one liquid phase anionic polymerization inhibitor. An example of an anionic polymerization inhibitor capable of acting as both a liquid phase and vapor phase stabilizer is trifluoroacetic acid. When such dual functional anionic polymerization inhibitors are used, it may be desirable to add a bit more of the inhibitor to the reaction vessel so as to account for the loss during the separation step.

Another exception is where the reaction phase stabilizer system further comprises a secondary anionic polymerization inhibitor that is or has the capacity to act as a vapor phase polymerization inhibitor or as a dual vapor-liquid phase polymerization inhibitor. As discussed in greater detail below, such secondary vapor phase and dual liquid-vapor phase anionic polymerization inhibitors include sulfur dioxide ($SO_2$), boron trifluoride ($BF_3$), nitric oxide (NO) or hydrogen fluoride (HF).

Generally speaking, the amount of the primary anionic polymerization inhibitor to be employed during the reaction phase should be from about 1 ppm to about 10,000 ppm, preferably, from about 5 ppm to about 6,000 ppm, more preferably from about 100 to about 5,000 ppm. Of course, the specific amount will vary depending upon the strength of the anionic polymerization inhibitor: in the case of an acid, the pKa value. Generally, it appears that the stronger the polymerization inhibitor, the lesser the quantity of anionic polymerization inhibitor needed. For example, a strongly acidic anionic polymerization inhibitor like sulfuric acid may be used in quantities in the lower end of the range, e.g., from about 1 to about 2000, preferably from about 5 to about 500, more preferably from about 10 to about 200 ppm, most preferably from about 10 to about 100 ppm. On the other hand, a comparatively weaker acid, like maleic acid, will be used towards the higher end of the range, generally from about 100 to about 5000, preferably from about 500 to about 4500, more preferably from about 1000 to about 4000, most preferably from about 2500 to about 3500 ppm based on the amount of the malonic acid ester or precursor thereof. Generally, the amount of anionic polymerization inhibitor to use can be determined by simple experimentation.

As indicated above, the reaction phase stabilizer system may also comprise, as an option, one or more secondary anionic polymerization inhibitors. These are generally anionic polymerization inhibitors that, on their own, do not appear to perform well as the sole or primary reaction phase anionic polymerization inhibitor, but which, when combined with the latter, provide an additive or synergistic stabilization effect to the overall crude product and reaction system. Suitable secondary anionic polymerization inhibitors include liquid phase, vapor phase, and dual liquid-vapor phase anionic polymerization inhibitors. Generally, secondary anionic polymerization inhibitors are also acids, especially, but not exclusively, those having an aqueous pKa of more than 2, more commonly more than 3, and/or having low conductivity in the non-aqueous medium. Exemplary secondary anionic polymerization inhibitors include, but are not limited to phosphoric acid; phosphorus pentoxide ($P_2O_5$); organic acids such as acetic acid, benzoic acid, fumaric acid, chloroacetic acid, cyanoacetic acid and mixtures thereof, especially acetic acid, benzoic acid or mixtures thereof; sulfur dioxide; nitric oxide; boron trifluoride; and hydrogen fluoride; as well as combinations of any two or more of the foregoing. As mentioned above, certain of these secondary anionic polymerization inhibitors, including sulfur dioxide, nitric oxide, boron trifluoride, and hydrogen fluoride, are or are also capable of acting as vapor phase anionic polymerization inhibitors. Additional exemplary secondary anionic polymerization inhibitors, including vapor phase inhibitors, and mixtures thereof are set forth in Malofsky et. al., U.S. Pat. No. 6,512, 023 B1, which is hereby incorporated herein in its entirety by reference.

The amount of the secondary anionic polymerization inhibitor to be employed, if present, will vary depending upon the strength of the same in inhibiting anionic polymerization and the nature of the stabilizer used. For example, the secondary anionic polymerization inhibitors will generally be employed at a level of from about 1 to about 500 ppm, preferably from about 10 to about 400 ppm, most preferably from about 15 to about 200 ppm. As with the primary anionic polymerization inhibitors discussed above, the strength of the inhibitor will also affect its level of use. For example, for the weaker acids such as acetic or benzoic acid, 25 to 400 ppm may be more appropriate whereas lesser amounts, such as from about 5 to about 200 ppm, preferably from about 15 to about 100 ppm will suffice for the stronger acids such as phosphoric acid. Similarly, when a vapor phase secondary anionic polymerization inhibitor is present, it will generally be employed at a level of from 1 to about 500 ppm, preferably from about 5 to about 200 ppm, more preferably from about 10 to about 100 ppm. For purposes of clarification, the amount of the secondary anionic polymerization inhibitor, when present, is in addition to the amount of the primary anionic polymerization inhibitor mentioned above.

As mentioned above, the reaction phase stabilizer system employed in the improved processes of the present invention may also include, and preferably does include, one or more free radical polymerization inhibitors. Suitable free radical inhibitors include, but are not limited to, the quinones and hindered phenols, especially the hydroquinones, hydroquinone monomethyl ether, catechol, pyrogallol, benzoquinones, 2-hydroxy benzoquinones, p-methoxy phenol, t-butyl catechol, butylated hydroxy anisole (BHA), butylated hydroxy toluene (BHT), t-butyl hydroquinones, 2,2"-methylene-bis (6-tertbutyl-4-methylephenol), and mixtures thereof. Generally speaking the amount of free radical inhibitor to be added to the system should be from about 100 to about 20,000, preferably from about 300 to about 10,000, more preferably from about 500 to about 5000 ppm, most preferably from about 800 to about 2000 ppm, based on the amount of malonic acid ester or, as appropriate, the adduct thereof. Generally, the optimal amount of free radical polymerization inhibitor to use for the particular system can be determined by simple experimentation.

Of course, a number of process variables may affect the amount and selection of the specific inhibitors to be employed in the reaction phase stabilizer system and are to be considered when formulating the stabilizer system. Process variables such as the reaction medium, the temperature at which the reaction is run, the reactants, the intended products, as well as the byproducts typically formed, can all affect the performance and selection of the various stabilizer(s) making up the reaction phase stabilizer system. For example, reaction processes employing or encountering higher temperatures seem to favor the stronger acids, like sulfuric acid; whereas, lower temperature processes seem to favor the comparatively weaker acids, like maleic acid.

Perhaps one of the most important variables affecting performance is the degree of dissociation of the selected polymerization inhibitors in the reaction mix, i.e., the adduct and stripping agent. In this respect, it is particularly important, if not paramount, that sufficient dissociation of the inhibitors, especially the primary anionic polymerization inhibitors, take place to manifest a sufficient degree of the acid effect on polymerization inhibition. Where the degree of dissociation in a particular reaction mix is of concern, one may enhance dissociation or overcome this issue by forming stock solutions of one or more of the selected polymerization inhibitors wherein the inhibitors are first dissociated or dissolved in a favorable media or solvent before being added to the reaction mix or, as appropriate, to the crude reaction product. Those skilled in the art will readily recognize suitable media and solvents for a given inhibitor or inhibitor combination as well as compatible media or solvents for the given reaction media or reactant mix. This can also be determined by simple experimentation. Exemplary media or solvents for forming such stock solutions are cyanoacetic acid, toluene and a combination thereof As discussed above, the improved process of the present invention may be further improved by the addition of a separation phase polymerization inhibitor during separation, purification and recovery, i.e., fractionation, of methylidene malonate. The separation phase stabilizer system comprises one or more primary anionic polymerization inhibitors, one or more secondary polymerization inhibitors, or a combination of the two, alone or in further combination with one or more free radical polymerization inhibitors, all as described above with respect to the components of the reaction phase stabilizer system. Indeed, while not necessary, it is to be appreciated that the separation phase stabilizer system may be the very same stabilizer system as the reaction phase stabilizer system. Similarly, except as noted below with respect to a vapor or dual liquid-vapor phase stabilizer, the amounts by which the individual polymerization inhibitors of the separation phase polymerization inhibitors are used is also consistent with that of the reaction phase stabilizer systems; though the tendency may be that their use is towards the middle and lower end of the ranges specified above so as not to subsequently affect the cure or polymerization characteristics of the purified monomer. Here, however, it is to be remembered that the amount is based upon the amount of methylidene malonate product expected and/or actually recovered from the separation process, not the malonate precursor material. Additionally, where the sole anionic polymerization inhibitor of the separation phase stabilizer system is a secondary anionic polymerization inhibitor, the amount to be employed will be consistent with the amount which would have been used if it were a primary anionic polymerization inhibitor as opposed to the lesser amounts used when a secondary anionic polymerization inhibitor is used to supplement the primary anionic polymerization inhibitor as set forth above.

When used, the amount of vapor phase or dual liquid-vapor phase anionic polymerization inhibitor to be employed in the improved fractionation process will vary depending upon the nature of the fractionation process itself. If the fractionation process is conducted in a closed system, one where there is no flow of air or other gas in or through the fractionation apparatus, or the collected volume is to be stored, whether as monomer or formulated material, then the vapor phase inhibitor will generally be employed at a level of from 1 to about 500 ppm, preferably from about 5 to about 200 ppm, more preferably from about 10 to about 100 ppm. However, where the fractionation process is conducted in an open system or under vacuum, one must account for the loss of the vapor phase stabilizer. Hence, in those processes, it is preferred to continuously introduce vapor phase stabilizer to the given system or apparatus, e.g., by bubbling, in order to maintain a concentration consistent with the levels mentioned for the closes systems. As note above, suitable vapor phase and dual liquid-vapor phase stabilizers include, trifluoroacetic acid, sulfur dioxide, boron trifluoride and hydrogen fluoride. Of course, the vapor phase stabilizer may be added to the liquid component as well as bubbled in, especially where the stabilizer is a dual liquid-vapor phase stabilizer.

As known in the art, the methylidene malonates formed by the improved process of the present invention may be employed in a number of organic syntheses and polymer chemistry applications. In particular, they are especially useful in the preparation of various adhesive and sealant applications including industrial, commercial and consumer adhesive and sealant applications as well as in skin bonding applications for human and animal skin bonding. In light of the benefit of the present invention, it is believed that these compositions are now commercially viable as cost effective and stable formulations can now be made.

EXAMPLES

Having described the invention in general terms, Applicants now turn to the following examples in which specific combinations of reactants and stabilizers as well as varied reaction times were evaluated. These examples are presented as demonstrating the surprising attributes of the improved processes of the present invention as well as the unexpected synergy resulting from the optional use of the combination of the anionic and free radical polymerization inhibitors. These examples are merely illustrative of the invention and are not to be deemed limiting thereof. Those skilled in the art will recognize many variations that are within the spirit of the invention and scope of the claims.

In conducting the following experiments, a preformed malonate adduct obtained from Virsol of Paris, France was employed. To recover the desired methylidene malonate from the malonate adduct, the following general stripping (reverse Diels-Alder) and distillation procedures were followed.

Reverse Diels-Alder: The adduct, maleic anhydride, and free radical polymerization inhibitor were charged to the reactor and the contents heated until a melt or liquid mixture was formed. Thereafter the anionic polymerization inhibitor was added to the melt: it was found that adding the anionic polymerization inhibitor prior to forming the melt led to charring of the materials. While maintaining the mixture as a melt, a mixer element was added to the reaction vessel and the vessel integrated into the overall apparatus. The condenser water was then turned on and the temperature of the reaction mix gradually elevated to 185° C. and held for a sufficient period of time, generally from about 2 to 4 hours, preferably from about 2¼ to 3¼ hours, to effectuate and ensure a complete, or nearly so, reverse Diels-Alder reaction. Although longer times can be used in an effort to increase yields, it is preferable to keep to the lower side of the timing so as to avoid the generation of impurities or deleterious side products and undesired reactions such as polymerization of the monomer.

Distillation: Typically, a two-step distillation process is employed, the first results in the recovery of crude product and the second the recovery of a purified distillate.

Crude Product: With the heat off, the product of the reverse Diels-Alder reaction is allowed to cool to <80° C., preferably <50° C., most preferably down to about 30° C., and the system is then subjected to a vacuum. The vacuum is applied slowly to control foaming of the reactor contents until a pressure of less than 10 mm Hg, preferably less than 5 mm Hg attained. Once the proper vacuum is attained, heat is applied to the contents of the reactor to initiate the crude distillation, e.g., by immersion of the reactor vessel in a hot oil bath, ~225° C. Because maleic anhydride remains in the crude product following the reaction and has a lower boiling point than the methylidene malonates, the first cut of the crude distillation is almost exclusively maleic anhydride. To prevent its condensation, including crystallization, in the distillation apparatus, it is preferred to heat the distillation pathway to ensure that the maleic anhydride will not condense until the collection vessel. Once material stops condensing over and the temperature of the system rises, the collection vessel containing the maleic anhydride is removed and replaced with a clean, prestabilized vessel. Thereafter, heating is resumed and continued until the distillation is completed. Heating is continued until the distillation is completed, generally when a reaction vessel temperature of 170° C. and a head temperature of 145° C., preferably with a vacuum of ~0.5-0.6 mm Hg is achieved. Completion may also be signified by, among other signs, the appearance of a whitish substance in the flow path. The actual distillation and head temperatures as well as the timing of the crude distillation will vary depending upon the specific methylidene malonate being isolated and the other components of the reaction mix. Thereafter, the heat is shut off and the remaining reactor mixture is allowed to cool while the system is maintained under vacuum. Once the reactor temperature reaches 100° C., the system is allowed to equilibrate to atmospheric pressure by bleeding air into the system, e.g., through the vacuum takeoff, preferably through a drierite (anhydrous calcium, sulfate) tube or a similar suitable anhydrous material containing tube. The crude product in the collection flask is then redistilled or stored for subsequent redistillation. Where the crude product is to be stored, it is preferably stabilized with additional polymerization inhibitors and stored under refrigerated conditions.

Redistillation: With no heat, the crude product (also referred to as the crude yield) is slowly subjected to a vacuum. During this step, any solvent, e.g., n-heptane, used in the extraction/separation step, if any, will come over and collect. When a vacuum of less than 0.5 mm Hg is attained, dry air is bled through the system and the vacuum trap emptied of any materials collected. Heat is then applied to the reactor contents at a moderate rate to initiate the initial redistillation. This distillation is allowed to continue until completed: completion may be signified by a drop in temperature and/or pressure.

Separation: Since no solvent or diluent medium is employed, separation is not necessary. However, if desired, separation may be employed advantageously as an intermediate step between the first and second steps of the two-step process to remove unwanted constituents from the reaction mix. Here the reaction mix may be washed with suitable solvents, e.g., diethyl ether, or dissolved in chloroform and washed with, e.g., saturated ammonium chloride and/or saturated sodium chloride solutions, depending upon the particular reactants and reaction processes followed: all as is known in the art.

Stabilization: In order to ensure good stability of the collected methylidene malonate during the crude distillation, it is desirable to add additional polymerization inhibitors to the crude product and the collection flask. Similarly, in the redistillation process(es), additional polymerization inhibitors are preferably added to the collection flask prior to commencing the distillation with the amount added based on the expected yield. The polymerization inhibitors added to the collection flasks may be the same as are added to the reaction mix during the stripping process or they may be other inhibitors known or found suitable for stabilizing the distilled monomer materials, especially those that would be suitable for use in the final products formulations such as trifluoroacetic acid (TFA) or a combination of $SO_2$ and sulfuric acid. The former has the added benefit of being relatively non-reactive towards the degradation products of the monomer as compared to the latter combination. This is particularly beneficial for long term stability. Generally speaking the amount of stabilizer in the collection flasks should be approximately 10 ppm anionic polymerization inhibitor and 100 ppm free radical inhibitor based on the anticipated yield of monomer: though higher and lower levels can be used depending upon the particular formulation as well known in the art or as can easily be determined by simple experimentation. Should it be found that the amount initially added to the flask was low, additional polymerization inhibitors should be added to raise the level up to enhance stability.

In performing the stripping and distillation processes, an apparatus comprising a resin kettle reactor vessel equipped with a distillation head—claisen adapter/temperature well/condenser, vacuum takeoff adapter and a 4-way cow receiver with adequately sized collection flasks and vacuum port was employed.

Examples E1-E4, Comparative Examples CE1-CE3

A series of reactions, with and without a diluent, were performed to strip and recover 1-ethoxycarbonyl-1-ethoxycarbonyl methylene oxycarbonyl ethane (formula I wherein $R^1$=—$CH_2CH_3$ and $R^2$=—$CH_2CO_2CH_2CH_3$) from the 2.1.2 adduct (11-ethoxycarbonyl-11-ethoxycarbonyl methylene oxycarbonyl-9,10-endoethano-9,10-dihydroanthracene). The quantity of adduct and maleic anhydride added to the reactor vessel for conducting the stripping reaction were as set forth in Table 1. Table 1 also identifies the various levels at which the anionic polymerization inhibitor (sulfuric acid) and the free radical polymerization inhibitor (hydroquinones (HQ)) were added, if present. The reactor was heated to 185° C. and the temperature held, and the reactor contents allowed to react, for 2¼ hours, unless otherwise noted.

Following reaction, the heat was removed and the contents of the reactor allowed to cool to <80° C. With the heat off, a vacuum was slowly applied to the system: slow enough to control foaming of the reactor contents. Once a vacuum of 0.1 to 0.4 mm Hg was attained with no further foaming, the reactor contents were heated to initiate distillation. Distillation continued to a reactor temperature of about 170° C. and a head temperature in the range of 140-150° C. Once distillation is completed, e.g., the formation of a whitish substance at the temperature well of the distillation head/claisen adapter oftentimes signified the later stage of the recoverable distillate, heating was discontinued and the contents of the system allowed to cool while maintaining vacuum. Once the temperature reached 100° C., the system was equilibrated to atmospheric pressure and the contents of the collection flask retained. The crude product was then stabilized to 10 ppm concentrated sulfuric acid and 100 ppm hydroquinone and stored under refrigerated conditions until redistillation.

Redistillation was effected in the same apparatus as the initial distillation: again the collection flask is prestabilized with sufficient sulfuric acid and hydroquinone to achieve a level of 10 ppm of the former and 100 ppm of the latter in the anticipated yield. Once again a vacuum was applied slowly to control foaming of the crude product, essentially trapped air. Once a vacuum of less than 0.5 mm Hg is achieved, dry air is bled through the system and the trap emptied. The reactor vessel is then heated at a moderate rate to begin distillation. Distilled product will begin to collect at a reactor temperature of 75-80° C. and a head temperature of ~30° C. Distillation is continued, collecting four evenly weighted fractions, to a reactor temperature of 215° C. and a head temperature of ~96-98° C. Distillation is completed when the reactor temperature drops from 215° C. to 205° C. and the head temperature drops from ~98° C. to ~92° C. If the amount of methylidene malonate recovered is found to be more than anticipated, additional stabilizers should be added to achieve the aforementioned 10 ppm and 100 ppm levels.

Comparative Example 1 (CE1) was performed in accordance with the present invention however maleic acid was used as the anionic polymerization inhibitor. Comparative Examples 2 and 3 (CE2 and CE3) were conducted in a similar manner except that CE2 included paraffin oil (300 ml) and CE3 included tricresyl phosphate (300 ml) as diluents in the stripping step which was conducted at 185° C. for 4.75 and 3.5 hours respectively.

As is evident from the results shown in Table 1, the process of the present invention provided a marked improvement in yield as compared to those systems using conventional diluents, even with the inventive stabilizer system. It is also believed that the products of the present invention were of greater purity as they produced a water-white product whereas the use of diluents in the stripping process resulted in products manifesting a visible coloration. Also, at the level used, it appeared that maleic acid was not suitable as a primary anionic polymerization inhibitor. Although more work is to be done, it is thought that the anionic polymerization inhibitor must be a stronger acid than maleic acid.

Based on our experiments, we have consistently been able to attain crude yields on the order of 60 to 90% and redistilled yields of pure or near pure 2.1.2 monomer of higher than 50%, generally higher than 60% on a consistent basis, without polymerization, or if an, very little: a feat not even remotely capable by the closest art. Indeed, as noted in the background section, Bru-Magniez achieved very inconsistent crude yields of only 21-71 percent, with poor purity, especially in terms of analogs, and, most disconcerting, with 25 to 100% of the product polymerizing either in the crude state or upon distillation time after time.

The crude yield was found, by gas chromatography and mass spectroscopy, to be a combination of the desired 2.1.2 monomer as well as minimal amounts, generally less than about 5% total, of diethyl methylidene (the 2.2 monomer) and di-(ethylmethyl) methylidene (the 2.1.1.2 monomer). Pure or nearly pure 2.1.2 monomer was attained through the redistillation process.

Example E3 demonstrated an alternate route to isolate the crude product from the reaction mix or mash. Here, the mash was placed in cheesecloth and the liquid materials allowed to separate by filtration and physical squeezing of the materials in the cloth. It is believed that a substantial quantity of the liquid monomer was left in the filtered mash, accounting for the low yield, which may have been recovered had an attempt been made to then conduct a distillation upon the remaining mash. Thus, while crude distillation is the preferred method for the initial recovery of the crude product from the reaction mix or mash, other methods such as filtration, with or without, distillation, may also be employed.

TABLE 1

| Example | 2.1.2 adduct (g) | Maleic anhydride (g) | H2SO4 (ppm) | HQ (ppm) | Maleic Acid (ppm) | Crude yield* (%) | Redistilled yield* (%) |
|---|---|---|---|---|---|---|---|
| E1 | 416 | 100 | 3000 | 3000 | — | 71.2 | 62.6 |
| E2 | 832 | 200 | 3000 | 3000 | — | 73.9 | 67.8 |
| E3** | 832 | 200 | 3000 | 3000 | — | 64.7 | 59.9 |
| E4*** | 416 | 100 | 3000 | 3000 | — | 103.2 | 97.7 |
| CE1 | 416 | 100 | — | 3000 | 3000 | 5.25 | n/a |

TABLE 1-continued

| Example | 2.1.2 adduct (g) | Maleic anhydride (g) | H2SO4 (ppm) | HQ (ppm) | Maleic Acid (ppm) | Crude yield* (%) | Redistilled yield* (%) |
|---|---|---|---|---|---|---|---|
| CE2 | 208 | 50 | 3000 | 3000 | | 87.3 | 71.6 |
| CE3 | 208 | 50 | 3000 | 3000 | | 76.9 | 55.4 |

*Based on the weight of the adduct
**product filtered after reaction
***>100% yield attributed to unreacted maleic anhydride and impurities distilling over Comparative Example CE1 demonstrates the impact of the use of weaker acids as anionic polymerization inhibitors in the practice of the present process. Generally, it has been found that the strength of the acid is proportional to the temperature at which the reaction, notably the stripping step, is run. The higher the temperature needed to melt the adduct and stripping agent, the stronger the acid needed.

While the present invention has been described with respect to aforementioned specific embodiments and examples, it should be appreciated that other embodiments utilizing the concept of the present invention are possible without departing from the scope of the invention. The present invention is defined by the claimed elements and any and all modifications, variations, or equivalents that fall within the spirit and scope of the underlying principles embraced or embodied thereby.

We claim:

1. An improved process for the production of methylidene malonates wherein the methylidene malonate is stripped from a malonate adduct wherein the improvement comprises heating the combination of the malonate adduct and stripping agent, wherein the stripping agent is maleic anhydride, in the absence of a diluent for said reaction and in the presence of an effective amount of a reaction phase polymerization inhibitor to a temperature at or above that at which at least one of the malonate adduct or the stripping agent melts and maintaining the temperature of the reaction mix at that temperature or another, non-pyrolytic temperature wherein the reaction mix remains in a liquid state for a sufficient period of time to strip the methylidene malonate from the malonate adduct.

2. The process of claim 1 wherein the combination of the malonate adduct and stripping agent is elevated to a temperature that is no more than 20° C. above that temperature at which at least one of the malonate adduct or stripping agent melt.

3. The process of claim 1 wherein the combination of the malonate adduct and stripping agent is elevated to a temperature that is no more than 10° C. above that temperature at which at least one of the malonate adduct or stripping agent melt.

4. The process of claim 1 wherein the reaction mix is elevated to a temperature at which both the malonate adduct and stripping agent melt.

5. The process of claim 1 wherein the reaction mix is elevated to a temperature above that at which one of the malonate adduct or stripping agent melts and the other is soluble or at least partially soluble therein.

6. The process of claim 1 wherein the malonate adduct is a diene or polynuclear aromatic platform on which the methylidene malonate is formed.

7. The process of claim 1 which further comprises the formation of the malonate adduct.

8. The process of claim 7 wherein the malonate adduct is formed by the reaction of a malonic acid ester with formaldehyde or a formaldehyde source and a diene in the presence of a catalyst and suitable reaction medium.

9. The process of claim 7 further comprising the step of isolating the malonate adduct before stripping the methylidene malonate.

10. The process of claim 1 wherein the reaction phase polymerization inhibitor comprises at least one primary anionic polymerization inhibitor, alone or in combination with one or more free radical polymerization inhibitor.

11. The process of claim 10 wherein the primary anionic polymerization inhibitor is a strong acid.

12. The process of claim 10 wherein the primary anionic polymerization inhibitor is selected from trifluoroacetic acid, sulfuric acid, maleic acid, perchloric acid and chlorosulfonic acid.

13. The process of claim 1 wherein the reaction phase polymerization inhibitor comprises at least one primary anionic polymerization inhibitor and one or more free radical polymerization inhibitors.

14. The process of claim 1 wherein the reaction phase stabilizer comprises a combination of at least one primary anionic polymerization inhibitor, at least one secondary anionic polymerization inhibitors and at least one free radical polymerization inhibitor.

15. The process of claim 1 further comprising the separation, purification and recovery of a purified or partially purified methylidene malonate from the crude reaction product.

16. The process of claim 15 wherein the separation, purification and recovery is conducted in the presence of a separation phase polymerization inhibitor.

17. The process of claim 16 wherein the separation, purification and recovery process comprises a sequence of at least two distillations on a crude methylidene malonate product with the first distillation comprising the isolation of the liquid crude methylidene malonate from any non-liquid components in the crude product and the second distillation comprising a re-distillation of the product of the first distillation.

18. The process of claim 16 wherein the separation, purification and recovery process comprises a sequence of at least three distillations on a crude methylidene malonate product with the first distillation comprising the isolation of the liquid crude methylidene malonate from any non-liquid components in the crude product, the second distillation comprising a re-distillation of the product of the first distillation and the third or subsequent distillation comprising the distillation of those fractions from the preceding distillation containing at least 50% by weight of methylidene malonate.

19. The process of claim 16 wherein the initial separation of the liquid methylidene malonate is by a method other than distillation and the method further comprises one or more additional purification steps, at least one of which is a distillation step.

20. The process of claim 16 wherein the separation phase polymerization inhibitor comprises at least one primary anionic polymerization inhibitor, at least one secondary anionic polymerization inhibitor, or a combination thereof.

21. The process of claim 20 wherein the separation phase stabilizer also includes one or more free radical polymerization inhibitors.

22. The improved process of claim 16 wherein at least a portion of the separation phase polymerization inhibitor is added to the collection vessel for the separated or purified or partially purified methylidene malonate before initiating the separation, purification and recovery process.

23. An improved process for the production of methylidene malonate which process involves the stripping of methylidene malonate from a malonate adduct using a stripping agent, wherein the stripping agent is maleic anhydride, and wherein the improvement comprises:
   a) heating the combination of the malonate adduct and stripping agent, wherein the stripping agent is maleic anhydride, to a temperature at or above that at which at least one of the malonate adduct of the stripping agent melts and maintaining the temperature of the reaction mix at that temperature or another, non-pyrolytic temperature wherein the reaction mix remains in a liquid state for a sufficient period of time to strip the methylidene malonate from the malonate adduct;
   b) stripping the methylidene malonate from the malonate adduct in the absence of a diluent for said stripping process and in the presence of one or more reaction phase polymerization inhibitors,
   c) adding one or more reaction phase polymerization inhibitors or one or more separation phase polymerization inhibitors to the crude liquid methylidene malonate product resulting from the stripping and subsequent separation of the same from the reaction mix,
   d) separating, purifying and recovering the purified or partially purified methylidene malonate product in the presence of one or more separation phase polymerization inhibitors, and
   e) adding one or more separation phase polymerization inhibitors to the recovered purified or partially purified methylidene malonate.

24. The process of claim 23 wherein the combination of the malonate adduct and stripping agent is elevated to a temperature that is no more than 20° C. above that temperature at which at least one of the malonate adduct or stripping agent melt.

25. The process of claim 23 wherein the combination of the malonate adduct and stripping agent is elevated to a temperature that is no more than 10° C. above that temperature at which at least one of the malonate adduct or stripping agent melt.

26. The process of claim 23 wherein methylidene malonate is stripped from the malonate adduct in the absence of a diluent for said reaction.

27. The process of claim 23 wherein the reaction mix is elevated to a temperature at which both the malonate adduct and stripping agent melt.

28. The process of claim 23 wherein the reaction mix is elevated to a temperature above that at which one of the malonate adduct or stripping agent melts and the other is soluble or at least partially soluble therein.

29. The improved process of claim 23 wherein the at least one reaction phase polymerization inhibitor is added to the malonate adduct prior to or concurrent with the stripping process.

30. The improved process of claim 1 wherein the reaction phase polymerization inhibitor comprises at least one anionic polymerization inhibitor having a pKa of 2.0 or less or comprising (a) at least one vapor phase and one liquid phase anionic polymerization inhibitor or (b) a dual liquid-vapor phase anionic polymerization inhibitor, alone or in combination with at least one free radical polymerization inhibitor.

31. The improved process of claim 23 wherein the reaction phase polymerization inhibitor comprises at least one anionic polymerization inhibitor having a pKa of 2.0 or less or comprising (a) at least one vapor phase and one liquid phase anionic polymerization inhibitor or (b) a dual liquid-vapor phase anionic polymerization inhibitor, alone or in combination with at least one free radical polymerization inhibitor.

* * * * *